United States Patent [19]

Bosserman et al.

[11] Patent Number: 5,124,023
[45] Date of Patent: Jun. 23, 1992

[54] CONTINUOUS REMOVAL OF POLYNUCLEAR AROMATICS FROM HYDROCARBON RECYCLE OIL

[75] Inventors: Paula J. Bosserman, Riverside; Vernon T. Taniguchi, Anaheim, both of Calif.

[73] Assignee: Union Oil Company of California, Los Angeles, Calif.

[21] Appl. No.: 527,570

[22] Filed: May 22, 1990

Related U.S. Application Data

[60] Continuation-in-part of Ser. No. 402,533, Aug. 31, 1989, and a continuation-in-part of Ser. No. 434,913, Nov. 8, 1989, which is a division of Ser. No. 276,627, Nov. 28, 1988, Pat. No. 4,915,843.

[51] Int. Cl.$^5$ .................. C10G 67/06; C10G 25/00; B01D 15/08
[52] U.S. Cl. .................. 208/99; 208/108; 208/310 R; 210/635; 210/656; 210/657; 210/659; 210/198.2
[58] Field of Search ............ 210/635, 656, 657, 659, 210/198.2; 585/400, 648, 825; 208/95, 99, 108, 310 R

[56] References Cited

U.S. PATENT DOCUMENTS

| | | | |
|---|---|---|---|
| 3,511,028 | 5/1970 | Saylor | 55/67 |
| 3,732,982 | 5/1973 | Dunnill et al. | 210/198 C |
| 4,255,607 | 3/1981 | Miyake et al. | 585/805 |
| 4,368,347 | 1/1983 | Carra et al. | 585/828 |
| 4,411,768 | 10/1983 | Unger et al. | 208/59 |
| 4,429,053 | 1/1984 | Ward | 208/111 |
| 4,447,315 | 5/1984 | Lamb et al. | 208/99 |
| 4,517,073 | 5/1985 | Ward | 208/111 |
| 4,542,254 | 9/1985 | Santacesaria et al. | 585/828 |
| 4,599,175 | 7/1986 | Yamamizu et al. | 210/635 |
| 4,618,412 | 10/1986 | Hudson et al. | 208/59 |
| 4,624,776 | 11/1986 | Long et al. | 208/302 |
| 4,775,460 | 10/1988 | Reno | 208/91 |
| 4,915,843 | 4/1990 | Taniguchi et al. | 210/635 |
| 5,024,749 | 6/1991 | Snyder | 210/198.2 |
| 5,045,209 | 9/1991 | Snyder | 210/635 |

FOREIGN PATENT DOCUMENTS

| | | | |
|---|---|---|---|
| 2440848 | 3/1976 | Fed. Rep. of Germany | 210/198.2 |
| 2065495 | 12/1980 | United Kingdom | 210/198.2 |

OTHER PUBLICATIONS

Unocal High Performance Technology No. 5, May 1988, pp. 1-4.
Ward, Applied Industrial Catalysis, 3: 337-360, Academic Press, Inc. (1984)
Barker et al., The Development and Applications of Preparative-Scale Continuous Chromatography *Separation Science and Technology*, 22 (8-10): 2011-2035 (1987).
Begovich et al., A Rotating Annular Chromatograph for Continuous Separation *AICHE Journal*, 30 (5): 705-710 (1984).
Begovich et al., A High-Capacity Pressurized Continuous Chromatograph *Separation Science and Technology*, 18 (12 & 13): 1167-1191, (1983).
Streat, *Ion Exchange for Industry*, Ellis Horwood Ltd., Chichester, England, pp. 424-442, (1988).
Canon et al., *Separation Science and Technology*, 15 (3): 655-678, (1980).
Canon et al., Operation of an Improved, Continuous Annular Chromatograph *Journal of Liquid Chromatography*, 1, (4): 427-441, (1978).
Howard et al., Separation of Sugars by Continuous Annular Chromatography, Oak Ridge National Laboratory, ORNL/TM-10318, (Aug. 1987) pp. 1-63.
Sisson et al., "Continuous Chromatography" *ChemTech*, Aug. 1988, pp. 498-502.
Taniguchi et al., *Journal of Metals*, 40 (11): 56, Annual Meeting (1988).
De Carli et al., Displacement Separation by Continuous Annular Chromatography, Extended Abstracts, American Institute of Chemical Engineers, 1988 Annual Meeting and BioChemE, p. 1D.

*Primary Examiner*—Ernest G. Therkorn
*Attorney, Agent, or Firm*—Gregory F. Wirzbicki; Shlomo R. Frieman

[57] ABSTRACT

Fused polynuclear aromatic compounds (PNAs) are continuously removed from a recycle oil stream in a hydrocracking process. An adsorption bed removes the PNAs from the recycle oil, a desorbing reagent removes the PNAs from the bed, and a regenerating agent regenerates the bed, all steps being performed simultaneously and continuously.

18 Claims, 6 Drawing Sheets

CONTINUOUS REMOVAL OF POLYNUCLEAR AROMATICS FROM HYDROCARBON RECYCLE OIL

CROSS-REFERENCE TO RELATED APPLICATIONS

This application is a continuation-in-part of application Ser. No. 07/402,533, filed Aug. 31, 1989; and a continuation-in-part of application Ser. No. 07/434,913, filed Nov. 8, 1989, which is a division of application Ser. No. 07/276,627, filed Nov. 28, 1988 (now U.S. Pat. No. 4,915,843), these documents being incorporated by reference in their entirety.

The present invention relates to a process and apparatus for continuously removing polynuclear aromatic compounds from a hydrocarbon fluid such as recycle oil in a hydrocracking process.

Petroleum refiners often produce desirable products (such as turbine fuel, diesel fuel, and other products known as middle distillate (or midbarrel) products, as well as lower boiling products, such as naphtha and gasoline) by catalytically hydrocracking high boiling hydrocarbons into product hydrocarbons of lower average molecular weight and boiling point. Hydrocracking is generally accomplished by contacting, in an appropriate reactor vessel, a gas oil or other hydrocarbon feedstock with a suitable hydrocarbon cracking catalyst under appropriate conditions, including an elevated temperature and an elevated pressure and the presence of hydrogen. Detailed descriptions of hydrocracking processes are contained in U.S. Pat. No. 4,429,053 and U.S. Pat. No. 4,517,073, these publications being incorporated herein in their entirety by reference.

A substantial proportion of the hydrocarbon products obtained from hydrocracking processes boil in a specified range, as for example, a gasoline boiling in the range of about 185° to about 420° F. Products boiling above about 420° F. are sometimes converted in another hydrocracking reactor to products having a boiling point below 420° F.

To increase the efficiency of the hydrocracking process, unconverted hydrocarbon oil exiting a hydrocracking reactor is recycled to one of the hydrocracking reactors for further processing. The recycled hydrocarbon oil is commonly called "recycle oil" and comprises aliphatic compounds and aromatic compounds, with generally less than half of the aromatic compounds being fused polynuclear aromatic compounds (PNAs). PNAs are any aromatic compound having two or more fused aromatic rings. Exemplary PNAs are coronenes and ovalenes.

The PNAs, and especially PNAs having at least about 5 fused rings, place constraints on the feed, operation, and profitability of the hydrocracking process. For example, catalyst deactivation and heat exchanger fouling are both attributed to PNAs.

Attempts, such as disclosed in U.S. Pat. No. 4,447,315 (Lamb et al.), have been made to remove PNAs from the hydrocracking process. Lamb et al. disclose a hydrocracking process wherein, prior to returning recycle oil to a hydrocracking zone, the recycle oil is passed through an adsorption zone to remove the PNAs present in the recycle oil. In the adsorption zone, an adsorbent is installed in one or more vessels, the vessels being in either series or parallel flow. Lamb et al. prefer parallel flow of the recycle oil through the adsorption zone so that, when one of the adsorption beds is spent by the accumulation of PNAs on the bed, the spent bed may be bypassed while continuing uninterrupted operation through the unspent bed. The spent adsorbent may then be regenerated or replaced.

There are drawbacks to Lamb et al.'s PNA removal process. First, the periodic discarding or regeneration of the spent adsorbent are both batch processes. Batch processes are undesirable in industrial procedures because they are generally labor intensive, tend to complicate the overall procedure, and are typically more expensive than a continuous process for performing the same function.

SUMMARY

The present invention provides a continuous process for removing PNAs from recycle oil in a hydrocracking process while continuously removing the PNAs from an adsorption bed. More particularly, the method entails simultaneously introducing separate streams of the recycle oil, a desorbing reagent, and a regenerator reagent proximate the entrance end of an adsorbent bed. The desorbing reagent comprises a liquid capable of removing the PNAs from the bed, and the regenerator reagent comprises a gas capable of regenerating the bed.

Each stream is introduced in a manner so that the recycle oil stream contacts a first portion of the bed, the desorbing reagent stream contacts a second portion of the bed, and the regenerating reagent stream contacts a third portion of the bed. While Simultaneously introducing the three streams, the portions of the bed contacted by each stream are sequentially changed so that substantially all the bed is sequentially contacted with the recycle oil stream, the desorbing reagent stream, and the regenerator reagent stream. The oil exiting the bed, which is substantially devoid of any PNAs, is recycled to a hydrocracking zone.

In addition, the desorbing reagent stream removes substantially all the PNAs adsorbed on the bed, and the regenerating reagent stream regenerates the bed. The bed is then ready for a repeat of this cycle.

DRAWINGS

The continuous PNA removal process and other features, aspects, and advantages of the present invention will become better understood with reference to the following description, appended claims, and accompanying drawings where like numerals refer to like elements and:

DETAILED DESCRIPTION OF THE INVENTION

Figure 1:
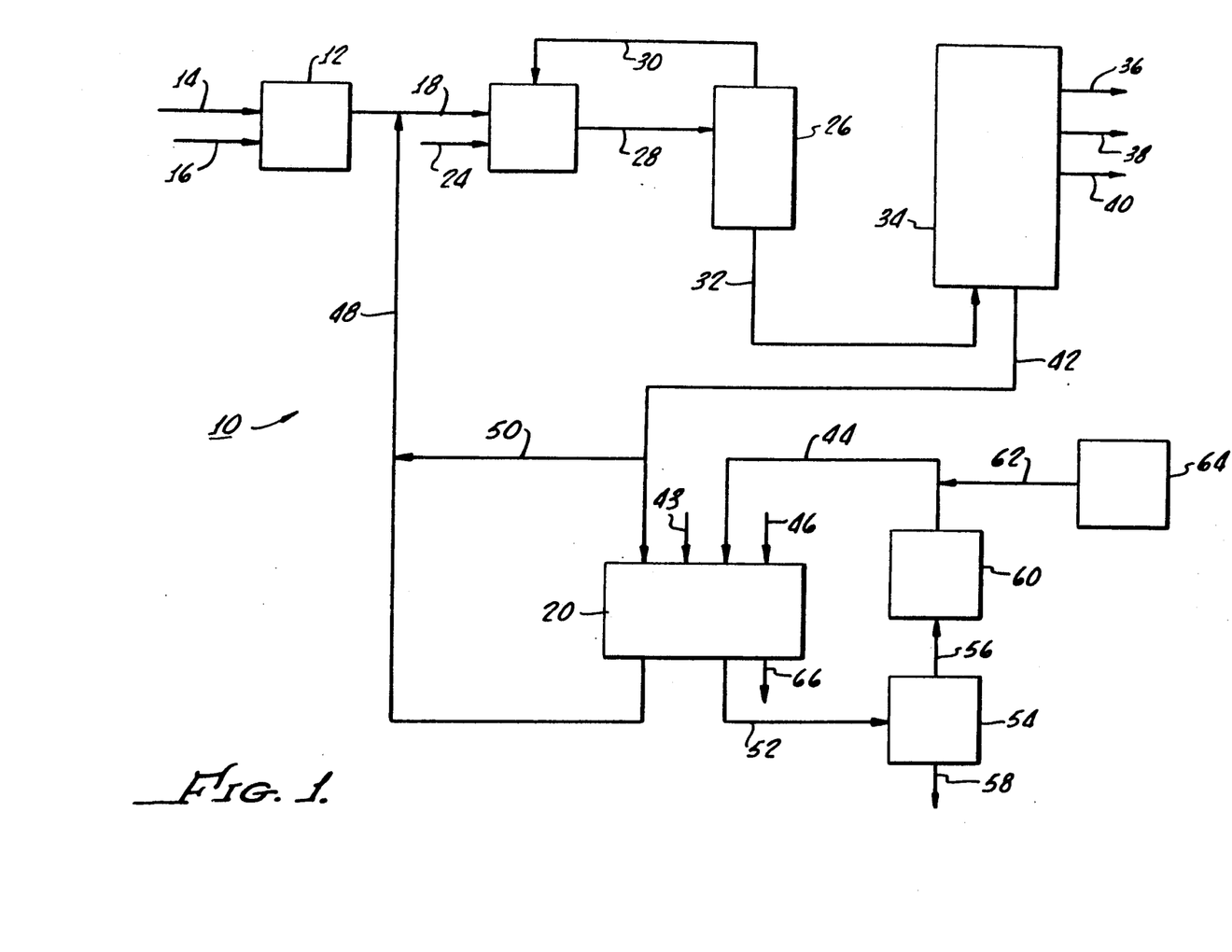
FIG. 1 is a schematic representation of a hydrocracking process embodying features of the present invention.
Figure 2:
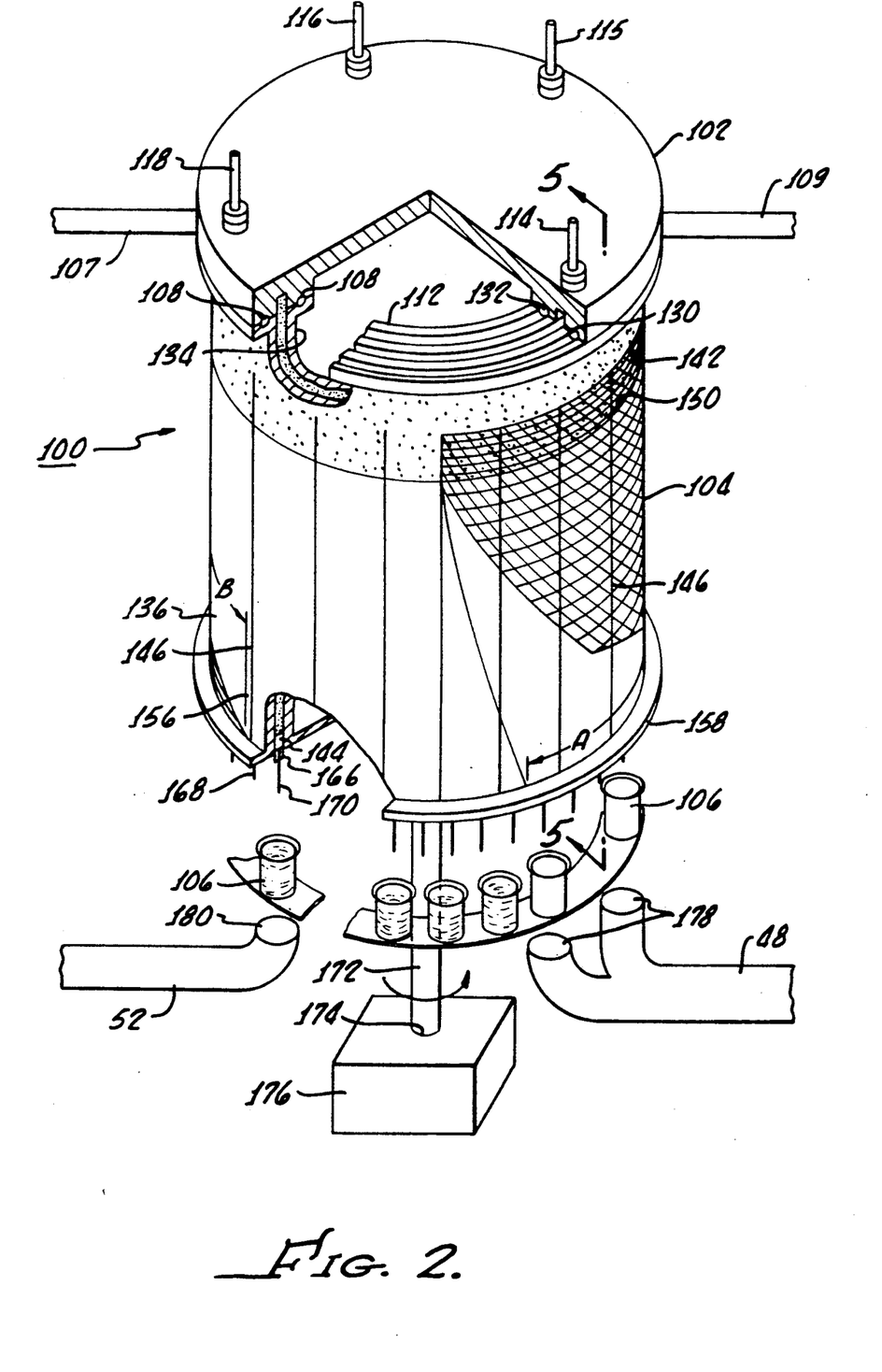
FIG. 2 is a perspective, front view of a continuous adsorption apparatus embodying features of the present invention.
Figure 3:
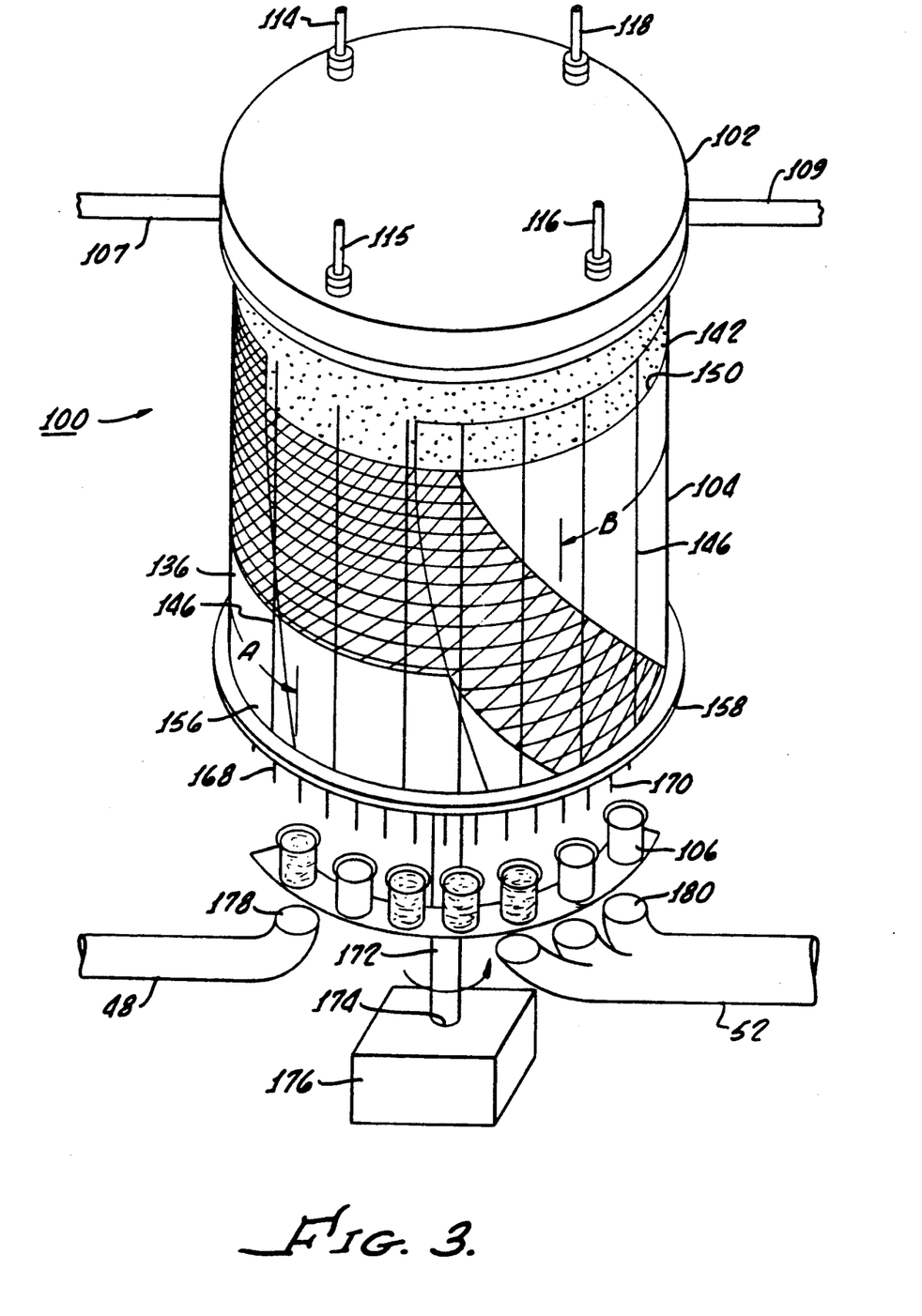
FIG. 3 is a perspective, rear view of the continuous adsorption apparatus of FIG. 2.

With reference to FIG. 1, the present invention provides a hydrocracking process 10 having an adsorption zone 20 for continuously removing PNAs from recycle oil. In one version of the invention as shown in FIGS. 2-5, the adsorption zone 20 is a continuous adsorption apparatus 100. As best seen in FIGS. 2-3, the adsorption apparatus 100 comprises a stationary inlet distributor manifold 102, a rotating annular column 104, and a plurality of stationary collector receptacles 106. The receptacles 106 are situated about the circumference of a circle beneath the annular column 104.

Figures 4, 5, 7:
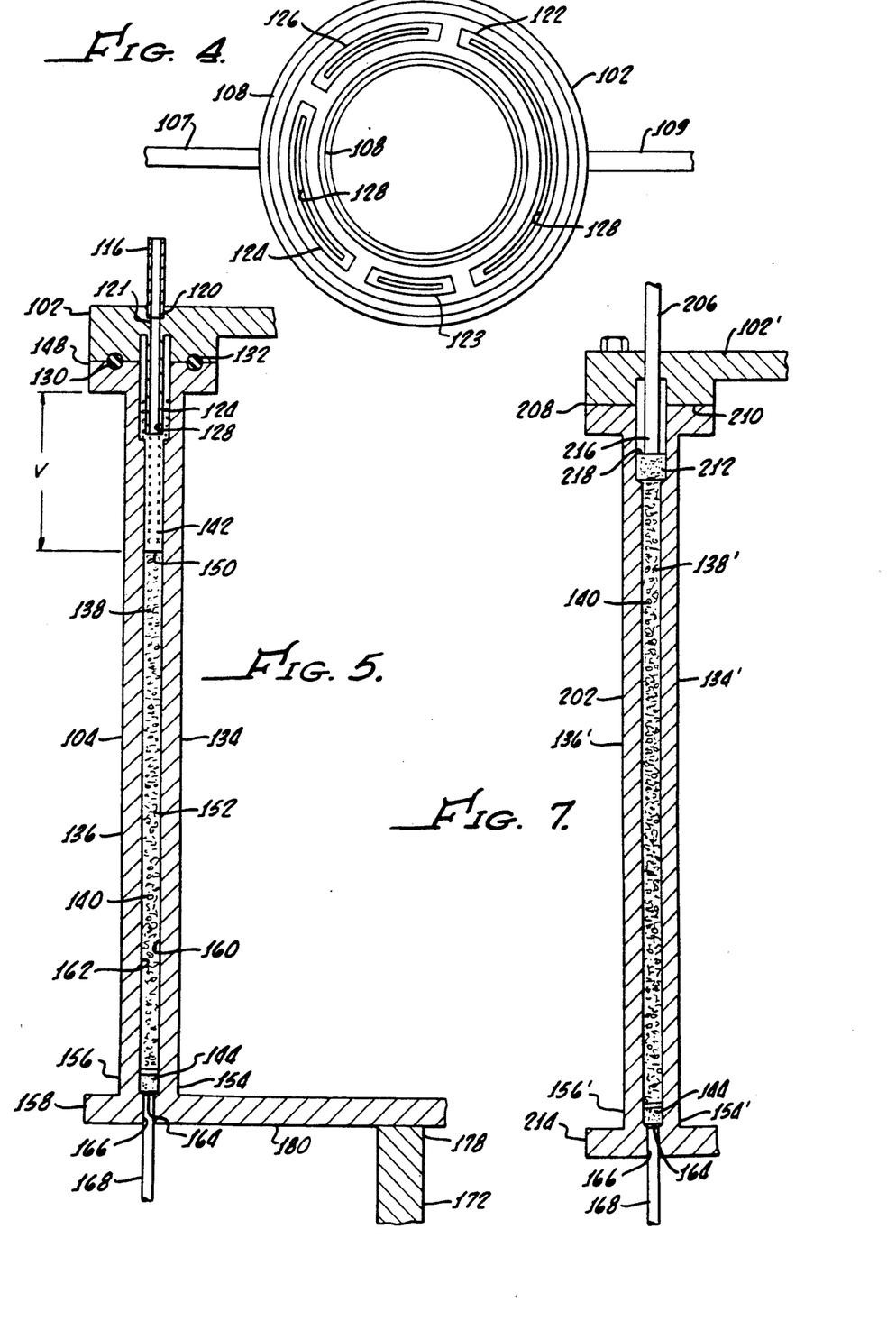
FIG. 4 is a bottom plan view, taken from FIG. 2, of the inlet distribution manifold 102 of the adsorption apparatus of FIGS. 2 and 3.
FIG. 5 is a partial cross-sectional view of the continuous adsorption apparatus along lines 5—5 of FIG. 2.
FIG. 7 is a partial cross-sectional view of the continuous HPLC apparatus along lines 7—7 of FIG. 6.

As shown in FIGS. 2 and 4, arms 107 and 109, which attach the distributor manifold 102 to stationary supporting columns (not shown), maintain the bottom surface 108 of distributor manifold 102 in tight physical contact with the upper surfaces 110 and 112 of the rotating annular column 104.

A recycle oil inlet tube 114, a purge reagent inlet tube 115, a desorbing reagent inlet tube 116, and a regenerator reagent inlet tube 118 conduct their respective recycle oil or reagent across the distributor manifold 102. (See FIG. 2-3.) The exit end 120 (shown in FIG. 5) of each of the inlet tubes 114, 115, 116, and 118 preferably terminates at the entrance 121 of a curved, elongated slot 128 that transverses each of distribution devices 122, 123, 124, or 126, respectively. (See FIG. 4.) The distribution device 122, 123, 124, or 126 are adapted to distribute their respective recycle oil or reagent through the slot 128 over a sector having an area greater than the cross-sectional area of its respective inlet tube 114, 116, and 118. Alternatively, one or more of the inlet tubes 114, 115, 116, and 118 can terminate in distribution devices (not shown) adapted to distribute its respective recycle oil or reagent through a series of nozzles (not shown) that are in fluid communication with the inlet tube 114, 115, 116, or 118, respectively.

The stationary inlet distribution manifold 102 is in O-ring contact 130 and 132 with the rotating annular particulate bed 104. (See FIGS. 2 and 5.) The O-rings 130 and 132 enable axial rotation of the annular column 104 relative to the inlet distributor manifold 102.

As best illustrated in FIG. 5, the rotating annular column 104 is defined by a cylindrical inner core 134 and a coaxial cylindrical exterior shell 136. Sandwiched in the annular space between the inner core 134 and the exterior shell 136 is an adsorption bed 138 composed of a chromatographic material or adsorbent 140, a chromatographically inert retaining layer 142, and a porous annular collector frit 144. The porous annular collector frit 144, which is porous substantially throughout its entire length and width, aids in maintaining the longitudinal integrity of the chromatographic bed 138.

Optionally, a plurality of annularly spaced, substantially vertical ribs 146 are also sandwiched between the inner core 134 and the exterior shell 136. (See FIG. 2.) These ribs 146 span the radial distance between the outer surface 160 of the inner core 134 and the inner surface 162 of the of the exterior shell 136 shown in FIG. 5. Preferably, the ribs 146 are in fluid tight contact with the outer surface 160 of the inner core 134 and the inner surface 162 of the of the exterior shell 136, and physically segment one portion of the bed 138 from another portion of the bed 138.

Regarding the inert retaining layer 142, the layer 142 is present in the annular space between the top 148 of the rotating annular particulate bed 104 and the upper edge 150 of the adsorbent 140. At least a portion of each distribution device 122, 123, 124, and 126 is submerged in the inert retaining layer 142. The depth of the chromatographically inert retaining layer 142 is sufficient to prevent substantially any disruption of the adsorbent 140 bordering the inert retaining layer 142 due to either (a) the introduction of the recycle oil or reagents through the distribution devices 122, 123, 124, and 126 or (b) the relative motion of the adsorbent bed 138 with respect to the stationary distribution devices 122, 123, 124, and 126.

An exemplary chromatographically inert retaining layer 142 is composed of glass beads. Preferably, the glass beads have a particle size sufficiently small so that the submerged portion of the distribution devices 122, 123, 124, and 126 are capable of horizontally passing through the glass beads without any significant impedance or any significant disruption of the adsorbent 140 proximate the retaining layer 142. In addition, the glass beads preferably have a particle size sufficiently large so that they remain a substantially separate layer atop the adsorbent 140 during use of the apparatus 100. Typically, the glass beads have an average particle size at least about two times as great as the average particle size of the adsorbent 140, and it is preferred that the particle size be within the range of about 20 to about 50 mesh.

With respect to the adsorbent 140, exemplary adsorbents include, but are not limited to, molecular sieves, silica, carbon, alumina, silica-alumina, magnesium silicate, cellulose acetate, and polystyrene. Preferably, the adsorbent 140 is selected from the group consisting of molecular sieves, silica, alumina, silica-alumina, magnesium silicate, with alumina (e.g., 100-200 mesh) and silica being the most preferred.

The moisture content of alumina affects the capability of alumina to separate the PNAs being removed from the recycle oil into distinct subclasses. In general, as the water content of the alumina increases up to about 5 weight percent, the ability of the alumina to separate PNAs into individual, specific PNA subclasses increases. However, at present there is little need for such selectivity. Accordingly, except for water present in the ambient atmosphere and which is taken up by the alumina, it is preferred that water not be added to the alumina. In this preferred embodiment, the water content of the alumina is typically about 0.01 to about 1 weight percent, and more preferably about 0.01 to about 0.5 weight percent.

As best viewed in FIG. 5, the radial relationship between the inner core 134 and the exterior shell 136 is maintained by permanently attaching (e.g., welding) the bottom end 154 of the inner core 134 and the bottom end 156 of the exterior shell 136 to a bottom plate 158. The annular thickness between the inner core 134 and the exterior shell 136 can be almost as large as the radius of the exterior shell 136. For example, the annular thickness can be such that the adsorption bed 138 occupies up to about 95 percent of the cross-sectional internal area of the exterior shell 136. However, the adsorption bed 138 typically occupies less than about 75 percent, and preferably about 1 to about 50 percent, of the internal cross-sectional area of the exterior shell 136. Specifically, the radial distance between the outer surface 160 of the inner core 134 and the inner surface 162 of the exterior shell 136 is usually between about 0.1 inch and about 10 feet, and more typically between about 1 inch to about 1 foot. However, the preferred radial distance is dependent on the anticipated output volume of material to be processed through the apparatus 100 when used as the adsorption zone 20 of FIG. 1.

The lower surface 164 of the porous annular collector frit 144 is preferably in fluid tight contact with the entrance end 166 of each collector tube 168. Below the exit ends 170 of the collector tubes 168 are the stationary collector receptacles 106, and below a portion of the collector receptacles 106 are entrances 178 to a return conduit 48, while under another portion of the collector receptacles 106 ar entrances 180 to a desorbing reagent-PNA transporting conduit 52. (See FIG. 2 and 3.)

As depicted in FIGS. 2, 3, and 5, the annular bed 104 is rotated by a coaxial shaft 172 having one end 174 attached to a motor 176 and another end 178 attached to the lower surface 180 of the bottom plate 158.

In accordance with a process employing the continuous adsorption apparatus 100 as the adsorption zone 20 in the hydrocracking process 10 of FIG. 1, a feedstock from a hydrotreating reactor is introduced into a first hydrocracking reactor 12 through a conduit 14. In addition, hydrogen is introduced into the first hydrocracking reactor 12 via a conduit 16. The effluent from the first hydrocracking reactor 12 is conveyed in a conduit 18 to a second hydrocracking reactor 22. Another conduit 24 feeds supplemental hydrogen to the second hydrocracking reactor 22.

The effluent from the second hydrocracking reactor 22 is in turn conveyed to a high pressure separator 26 via a conduit 28. Two effluent streams, namely, a gaseous hydrogen-rich effluent and a condensed, normally liquid, hydrocarbon effluent, leave the separator 26. The gaseous hydrogen-rich effluent is returned to the second hydrocracking reactor by a conduit 30, and the condensed, normally liquid, hydrocarbon effluent is passed through a conduit 32 to a fractionator 34.

The fractionator 34 separates the incoming hydrocarbons into various products such as gasoline, turbine fuel, and diesel fuel, each product leaving the fractionator 34 through its respective take-off conduit 36, 38, or 40. In addition, a high boiling residual material (typically having a boiling point above about 650° F. and commonly called recycle oil or fractionator bottoms or botts) is directed by a conduit 42 from the fractionator 34 to the continuous adsorption zone 20. Also, a purge reagent stream, a desorbing reagent stream, and a regenerator reagent stream are fed into the adsorption zone 20 by means of conduits 43, 44, and 46, respectively.

With reference not to FIGS. 2–5, the recycle oil stream, the purge reagent stream, the desorbing reagent stream, and the regenerator reagent stream are simultaneously fed into the apparatus 100 while the adsorption bed 138 is rotated counterclockwise, the time per rotation being generally less than about 2 days. Preferably, bed 138 completes one rotation within about 1 to about 35 hours, and more preferably within about 5 to about 20 hours.

The recycle oil stream, the purge reagent stream, the desorbing reagent stream, and the regenerator reagent stream are respectively and simultaneously fed into the apparatus 100 through the recycle oil inlet tube 114, the purge reagent inlet tube 115, the desorbing reagent inlet tube 116, and the regenerator reagent inlet tube 118.

The purge reagent, which is a fluid, and preferably an inert gas, is employed to prevent the recycle oil from entering or becoming commingled with the desorbing reagent stream. In particular, the purge reagent stream removes substantially all of the residual aliphatic and monoaromatic compounds from the bed 138 so that these residual compounds do not become incorporated into the desorbing reagent stream flowing through the bed 138.

The desorbing reagent comprises a liquid capable of removing the PNAs from the bed 138. Typically, the desorbing reagent is capable of solubilizing the PNAs. Exemplary desorbing reagents include, but are not limited to, light cycle oil from a fluidized catalytic cracking (FCC) reactor, N,N-dimethylformamide, aromatic solvents (e.g., benzene and toluene), halogenated hydrocarbon solvents (e.g., methylene chloride, chloroform, carbon tetrachloride, carbon tetrafluoride, trichloroethane, and hexacloroethane), ethers (e.g., dimethyl ether, diethyl ether, and dipropyl ether), ketones (e.g., acetone and methyl ethyl ketone), and alcohols (e.g., methanol, ethanol, and propanol). In general, the light cycle oil boils in the range of about 450° to about 700° F. and comprises up to about 50 volume percent of compounds selected from the group consisting of monoaromatic compounds and aromatic compounds containing two to about three fused rings, the remainder of the light cycle oil being aliphatic compounds.

The regenerator reagent is capable of regenerating the bed 138, i.e., returning the adsorbent 140 to substantially the same form it possessed prior to contacting the adsorbent 140 with the PNA-containing recycle oil. An exemplary regenerator reagent is a heated inert gas (e.g., nitrogen, argon, etc.), the gas being at a temperature preferably in the range of about 100° to about 300° C., and more preferably about 150° to about 250° C. In those embodiments of the invention where the adsorbent 140 has an added water content, the regenerator reagent preferably also has a water vapor content sufficient to restore the original moisture content to the adsorbent 140. Typically, the same inert gas is employed as the purge reagent stream and the regenerator reagent stream.

The recycle oil stream, the purge reagent stream, the desorbing reagent stream, and the regenerator reagent stream simultaneously and respectively exit the distributor manifold 102 through the recycle oil distributor device 122, the purge reagent distributor device 123, the desorbing reagent distributor device 124, and the regenerator reagent distribution device 126, respectively. The recycle oil stream is introduced into the rotating annular column 104 by the recycle oil distributing device 122 over a sector that generally spans at least about 70° (or at least about 20 percent of the horizontal cross-sectional area or extent of the bed 138). More typically and preferably, the recycle oil stream is introduced into the annular column 104 over a sector of about 90° to about 180° (or about 25 to about 50 percent of the horizontal cross-sectional extent of the bed 138).

With respect to the purge reagent stream, this stream is usually introduced into the rotating annular column over a sector spanning up to about 55° (or up to about 15 percent of the horizontal cross-sectional extent of the adsorption bed 138). Preferably, the purge reagent stream sector covers about 5° to about 45° (or about 1 to about 13 percent of the horizontal cross-sectional extent of the adsorption bed 138).

In general, the desorbing reagent stream and the regenerator reagent stream are each introduced into the rotating annular column 104 over adjacent, substantially separate sectors. Each of these sectors covers at least about 5° (or at least about 1 percent of the horizontal cross-sectional extent of the adsorption bed 138). Preferably, the desorbing reagent and the regenerator reagent are each introduced over substantially separate sectors of about 10° to about 120° each (or each sector spanning at least about 3 to about 35 percent of the horizontal extent of the adsorption bed 138), and more preferably over sectors of about 35° to about 90° each (or each sector covering at least about 10 to about 25 percent of the horizontal extent of the adsorption bed 138).

When introduced into the annular column 104, the recycle oil stream, the purge reagent stream, the desorbing reagent stream, and the regenerator reagent stream separately enter the inert retaining layer 142 and proceed downwardly into the adsorbent 140. To prevent any disruption in the steady state nature of the continuous process performed by the adsorption apparatus 100, it is preferred that all streams be introduced into the annular column 104 at substantially the same flux rate (volume/time/area). When employed, the annularly spaced ribs 146 aid in maintaining the process in a steady state and counteract the effects of lateral diffusion and band broadening.

Initially, the adsorbent 140 is either present in a regenerated or activated form or is regenerated or activated. When it is necessary to first activate the adsorbent 140, the adsorbent 140 is activated either before or after being placed in the adsorption bed 138. When activated in the bed 138, prior to introducing the recycle oil, the purge reagent (if different from the regenerator reagent), and the desorbing reagent into the bed 138, the regenerator reagent is first passed through the regenerator reagent distribution device 126 and through the adsorbent 140 until substantially 100 percent activation is achieved.

The PNAs present in the recycle oil are adsorbed onto the adsorbent 140 in the rotating bed 138 while the aliphatic compounds and the monoaromatic compounds in the recycle oil pass through the bed 138 and are collected in a portion of the stationary collecting devices 106. In steady state operation, the aliphatic and aromatic compounds tend to exit the bed over a substantially constant circumferential distance A.

Generally, sufficient recycle oil stream is introduced into the adsorbent 140 so that less than 100 percent of the total adsorbent capacity of the bed 138 is occupied by the PNAs. To prevent premature passage of the PNAs from the bed 138, it is preferred that the PNAs occupy less than about 95 percent, and more preferably less than 90 percent, of the total adsorbent capacity of the bed 138. On the other hand, in order to avoid wasting adsorbent capacity, typically at least about 25 percent, and preferably at least about 50 percent, of the total adsorbent capacity is occupied by the PNAs.

As noted above, the purge stream is employed to remove substantially all of the residual aliphatic and monoaromatic compounds from the bed 138 so that these residual compounds do not become incorporated into the desorbing reagent stream.

In an alternative embodiment of the invention where the purge stream is not employed, this separation is simulated by appropriately spacing adjacent ribs 146, e.g., making the maximum distance between adjacent ribs 146 less than the circumferential distance separating the recycle oil distributor device 122 and the desorbing reagent distributor device 124. To increase the separation between the aliphatic and monoaromatic compounds descending through the bed 138 and the following desorbing reagent stream, it is preferred that the maximum distance between neighboring ribs 146 be less than one-half, and more preferably less than one third, the circumferential distance separating the the recycle oil distributor device 122 and the desorbing reagent distributor device 124. Of course, the above spacing between adjacent ribs 146 can be also employed in conjunction with the use of the purge stream.

With respect to the desorbing reagent stream, this stream, as previously mentioned, comprises a liquid capable of removing the PNAs from the bed 138. Accordingly, as the desorbing reagent passes through the bed 138, the desorbing reagent removes the PNAs from the adsorbent 140, and both the desorbing reagent and PNAs are jointly collected in another separate portion of the receiving devices 106. When the PNA separation process achieves steady state operation, the desorbing reagent-PNA combination generally exits the bed 138 over a substantially constant circumferential distance B.

Any residual desorbing reagent present in the adsorbent bed 138 is then removed from the bed 138 by the regenerator reagent stream which sequentially follows the desorbing reagent through the adsorbent 140. The regenerator reagent stream also returns the adsorbent 140 to its original regenerated or activated condition so that the adsorbent 140 is ready to remove PNAs from the recycle oil introduce into the rotating annular column 104 during the following cycle.

Thus, in operation, at any point in time, some of receptacles 106 (typically those receptacles 106 positioned within the circumferential distance A under where the the aliphatic and monoaromatic compounds exit bed 138) are collecting aliphatic and monoaromatic compounds, and some (typically those receptacles 106 positioned within the circumferential distance B under where the desorbing reagent-PNA combination exit the bed 138) are collecting PNAs. Since the circumferential locations and distances where the aliphatic and monoaromatic compounds and desorbing reagent-PNA combination exit the bed 138 each remain substantially constant under steady state operating conditions, it is preferred that the number and identity of the individual receptacles 106 collecting the aliphatic and monoaromatic compounds as well as the number and identity of the individual receptacles 106 collecting the PNAs remain essentially the same during the operation of the adsorption apparatus 100.

The collector receptacles 106 containing the separately collected (a) aliphatic and monoaromatic compounds and (b) desorbing reagent-PNA combination are periodically emptied into the return conduit 48 and the desorbing reagent-PNA transporting conduit 52, respectively. For example, the collector receptacles 106 can be equipped with a drain valve (not shown) that is activated by a level detection device (not shown).

Accordingly, each time the liquid in a collector receptacle 106 reaches a predetermined level, the level detector sends a signal that causes the drain valve of that receptacle 106 to open, thereby draining any aliphatic and aromatic compounds or any desorbing reagent-PNA combination present in the receptacle 106 into the return conduit 48 or the desorbing reagent-PNA transporting conduit 52, respectively.

As indicated in FIG. 1, the return conduit feeds the separately collected aliphatic compounds and monoaromatic compounds into the conduit 18 that, as noted above, also delivers the effluent from the first hydrocracking reactor 12 to the second hydrocracking reactor 22. If necessary to increase the pressure under which these recycled compounds are introduced into the conduit 18, a pump (not shown) can be used to boost the return pressure. In addition, a portion of the recycle oil can optionally bypass the adsorption zone 20 and be returned to the second hydrocracking reactor 22 via a conduit 50 that connects with the return conduit 48 carrying the recycled aliphatic compounds.

With reference to the separately collected desorbing reagent-PNAs combination, the desorbing reagent-PNA transporting conduit 52 directs this combination to a distillation apparatus 54. The distillation apparatus 54 separates the PNAs from the desorbing reagent, the desorbing reagent leaving the distillation apparatus 54 via a conduit 56 and the PNAs being periodically removed from the distillation apparatus via a conduit 58.

The conduit 56 delivers the desorbing reagent, in vapor form, to a condenser 60 which returns the desorbing reagent to liquid form. The liquid desorbing reagent is then recycled to the continuous adsorption zone 20 by means of the conduit 44. Any make-up desorbing reagent is added to conduit 44 through a make-up conduit 62.

One source of make-up desorbing reagent is a fluidized catalytic cracking (FCC) reactor 64. The FCC reactor 64 is generally also present in an oil refinery containing the hydrocracking process 10. In fact, the PNAs removed from the distillation apparatus 54 can be added to the feedstock of the FCC reactor 64 wherein the they undergo condensation reactions and contribute to the coke formed on the catalyst present in the FCC reactor 64. The coke is subsequently pyrolyzed in the catalyst regeneration step of the FCC process, with the generated heat being used to volatilize feed entering the FCC reactor 64.

The regenerating reagent exiting the adsorption bed 138 is permitted to vent to the atmosphere, e.g., via conduit 66. However, the regenerating reagent can optionally be collected for reuse or treatment.

Figure 6:
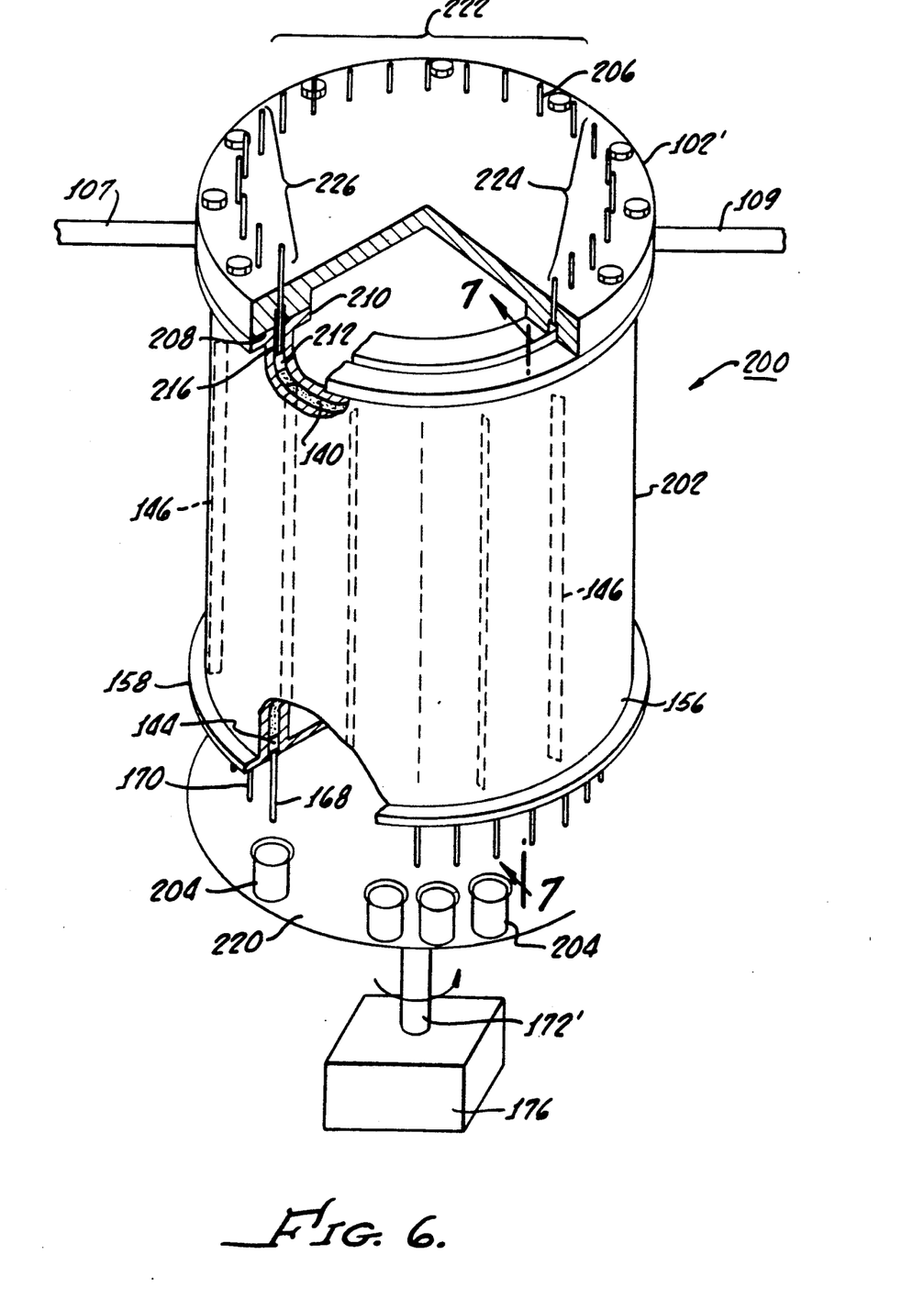
FIG. 6 is a perspective view of a continuous high performance liquid chromatography (HPLC) apparatus embodying features of the present invention.
Figure 8:
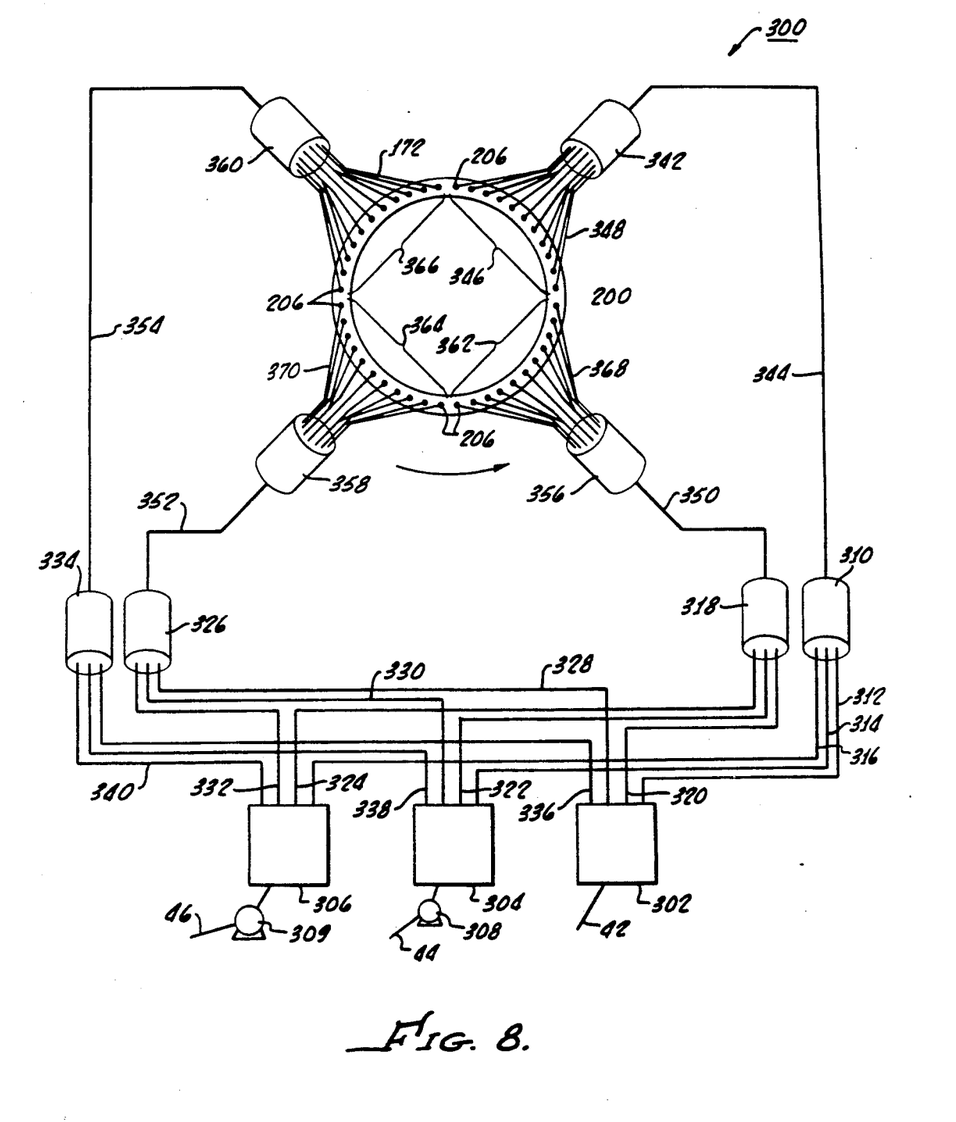
FIG. 8 is a schematic representation of a continuous HPLC system embodying features and of the present invention.

In another version of the present invention as shown in FIGS. 6-8, a continuous HPLC apparatus 200 is employed in the adsorption zone 20. The HPLC apparatus 200 has some features in common with the continuous adsorption apparatus 100 of FIGS. 2-5. Accordingly, to avoid repetition, the same numbers are used in FIGS. 2-8 to designate the same parts and primed numbers are used in FIG. 6-8 to designate similar parts.

As best viewed in FIGS. 6-7, the HPLC apparatus 200 comprises a stationary inlet distributor manifold 102', a stationary annular column 202, and a plurality of rotating collector receptacles 204. A plurality of annularly positioned inlet tubes 206 conduct fluids across the stationary inlet distributor manifold 102'. The stationary inlet distributor manifold 102' is maintained in fluid tight contact with the stationary annular column 202 by means of bolted gasket seals 208 and 210. Both the inlet distribution manifold 102' and the annular column 202 are maintained stationary with respect to the rotating collector receptacles 204 by means of the arms 107 and 109 connected to the manifold 102' by stationary columns (not shown).

The stationary annular column 202, like the rotating annular column 104, is defined by a cylindrical inner core 134' and a coaxial cylindrical exterior shell 136'. (See FIG. 7.) Sandwiched between the inner core 134' and the exterior shell 136' is a chromatographic bed 138' composed of the adsorbent 140, a porous annular distributor frit 212, the porous annular collector frit 144, and (optionally) the annularly spaced, substantially vertical ribs 146. The porous annular distributor frit 212, as in the case of the porous annular collector frit 144, is porous substantially throughout its entire length and width, with both frits 144 and 212 helping to maintain the longitudinal integrity of the chromatographic bed 138'. The radial relationship between the inner core 134' and the exterior shell 136' is maintained by permanently attaching the bottom end 154' of the inner core 134' and the bottom end 156' of the exterior shell 136' to a flange 214. (See FIG. 7.)

The annular thickness between the inner core 134' and the exterior shell 136' is the same as discussed above with respect to the adsorption apparatus 100.

The exit end 216 of each reagent inlet tube 206 physically contacts the upper surface 218 of the porous annular distributor frit 212. Preferably, each exit end 216 of the reagent inlet tubes 206 is in fluid tight contact with the upper surface 218 of the distributor frit 212. The lower surface 164 of the porous annular collector frit 144 contacts the entrance end 166 of each collector tube 168 as noted in the case of the adsorption apparatus 100. However, proximate the exit ends 170 of the collector tubes 168 are the rotating collector receptacles 204.

As depicted in FIG. 6, the collector receptacles 204 sit on a carousel 220 that is rotated by a shaft 172' by means of a motor 176.

It is generally desirable to use the HPLC apparatus 200 when the recycle oil stream, the desorbing reagent stream, and the regenerator reagent stream are each fed into the adsorption zone 20 at a pressure of at least about 100 psig each. More typically, when the HPLC apparatus is employed, each stream is introduced into the adsorption zone 20 at a pressure of about 500 to about 5,000 psig, and preferably at a pressure of about 800 to about 3,500 psig.

Referring to FIG. 8, an exemplary continuous HPLC arrangement 300 comprises the continuous HPLC apparatus 200, a recycle oil stream source 302, a desorbing reagent stream source 304, and a regenerator reagent stream source 306. The recycle oil source 302 is feed by conduit 42 of FIG. 1, the desorbing reagent source 304 is fed by conduit 44, and the regenerating reagent source 306 is fed by conduit 46. Pumps 308 and 309 increase the delivery pressure of the desorbing reagent and the regenerator reagent, respectively, delivered to the desorbing reagent source 304 and regenerator reagent source 306. (See FIG. 8.)

A first intake multiposition valve 310 is in fluid communication with the recycle oil stream source 302, the desorbing reagent stream source 304, and the regenerator reagent stream source 306 by conduits 312, 314, and 316, respectively. In an analogous fashion, a second intake multiposition valve 318 is in fluid communication with the recycle oil stream source 302, the desorbing reagent stream source 304, and the regenerator reagent stream source 306 by conduits 320, 322, and 324, respectively. A third intake multiposition valve 326 is in fluid communication with the recycle oil stream source 302, the desorbing reagent stream source 304, and the regenerator reagent stream source 306 by conduits 328, 330, and 332, respectively. Similarly, a fourth intake multiposition valve 334 is in fluid communication with the recycle oil stream source 302, the desorbing reagent stream source 304, and the regenerator reagent stream source 306 by conduits 336, 338, and 340, respectively.

The first, second, third, and fourth intake multiposition valves 310, 318, 326, and 334, respectively, are also in fluid communication with the continuous HPLC apparatus 200. In particular, the first intake multiposition valve 310 is connected to a first distributor multiposition valve 342 by a conduit 344. The first quadrant distributor multiposition valve 342 is in turn connected to a first quadrant 346 of the inlet tubes 206 via a plurality of first quadrant distributor conduits 348. Similarly, the second, third, and fourth intake multiposition valves 318, 326, and 334 are connected by conduits 350, 352, and 354, respectively, to their respective second, third, and fourth quadrant distributor multiposition valves 356, 358, and 360. The second, third, and fourth quadrant distributor multiposition valves 356, 358, and 360 are, in turn, connected to the inlet tubes 206 in their respective second, third, and fourth quadrants 362, 364, and 366 by a plurality of second, third, and fourth quadrant distributor conduits 368, 370, and 372, respectively.

Generally, the operation of the hydrocracking process 10, except for the adsorption zone 20, is the same when either the continuous apparatus 100 of FIG. 2-5 or the HPLC apparatus 200 of FIGS. 6-8 is employed. Similarly, when the HPLC apparatus 200 is used, the adsorbent 140 of the adsorbent bed 138' (as illustrated in FIGS. 6-7) is, when necessary, also regenerated or activated before or after being placed in the adsorption bed 138'. When activated after being placed in the bed 138', only the regenerator reagent stream is initially passed through substantially all of the inlet tubes 206 and through the bed 138' until substantially all of the adsorbent 140 in the adsorption bed 138' is activated.

The recycle oil stream, the desorbing reagent stream, and the regenerator reagent stream are then passed in a predetermined progression through the first, second, third, and fourth quadrant intake multiposition valves 310, 318, 326, and 334, respectively, and through the first, second, third, and fourth quadrant distribution multiposition valves 342, 356, 358, and 360, respectively. The intake multiposition valves 310, 318, 326, and 334 and distributor multiposition valves 342, 356, 358, and 360 are synchronized or programmed (e.g., by a computer) so that each stream enters the HPLC apparatus 200 through a substantially sequential discrete, separate, and continuous grouping of inlet tubes 206. Specifically, as noted in FIG. 6, distinct groupings of the inlet tubes 206 form a recycle oil stream grouping 222 that introduces the recycle oil into the HPLC apparatus 200, a desorbing reagent stream grouping 224 that introduces the desorbing reagent into the HPLC apparatus 200, and a regenerator reagent stream grouping 226 that introduces the regenerator reagent into the HPLC apparatus 200.

However, in a preferred embodiment, the regenerator reagent is also introduced into the HPLC apparatus 200 through a substantially sequential discrete, separate, and continuous grouping (not shown) of inlet tubes 206 between the recycle oil stream grouping 222 and the desorbing reagent stream grouping 224, the portion of the regenerator reagent so introduced functioning as a purge reagent stream.

Returning to FIG. 8, the sequentially synchronized first, second, third, and fourth intake multiposition valves 310, 318, 326, and 334 and the sequentially synchronized first, second, third, and fourth distributor multiposition valves 342, 356, 358, and 360 are further computer programmed so that the introduction of the recycle oil stream, the desorbing reagent stream, and the regenerator reagent stream into the adsorption bed 138' through their respective grouping 222, 224, or 226 of inlet tubes 206 is sequentially advanced counterclockwise as illustrated in FIG. 6. The collector receptacles 204 are also rotated or advanced in a counterclockwise direction at substantially the same annular velocity as the annular advancement of the separate recycle oil stream grouping 222, desorbing reagent stream grouping 224, and regenerator reagent stream grouping 226 of inlet tubes 206.

Generally, in the continuous HPLC embodiments of the invention, the percent of the total absorbant capacity of the absorbent 140 occupied by the PNAs, the sectors over which the recycle oil and reagents are introduced into the apparatus 200, the time per rotation, and the circumferential spacing between adjacent ribs 146 are the same as in the case of the adsorption apparatus 100. (See FIG. 6 and 7.)

Accordingly, the PNAs present in the recycle oil are adsorbed onto the adsorbent 140 in the stationary bed 138' while the aliphatic compounds and the monoaromatic compound-s in the recycle oil pass through the bed 138' and are collected in a portion of the rotating collector receptacles 204. In addition, as the desorbing reagent passes through the bed 138', the desorbing reagent removes the PNAs from the adsorbent 140, with both the desorbing reagent and PNAs being jointly collected in another separate portion of the collector receptacles 204.

Thus, in operation, at any point in time, some of rotating receptacles 204 are collecting aliphatic and monoaromatic compounds, and some are collecting PNAs. Although the circumferential locations at which the aliphatic and monoaromatic compounds exiting the HPLC apparatus 200 change during steady state operation, the circumferential distances over which these substances exit the HPLC apparatus 200 remains substantially constant. Since it is preferred that the carousel 220 annularly advance the receptacles at substantially the same annular velocity that the introduction of the recycle oil stream and reagent streams is advanced, and accordingly at the same annular velocity that the exiting substances are advances, it is also preferred that the number and identity of the individual receptacles 204 collecting the aliphatic and monoaromatic compounds as well as the number and identity of the individual receptacles 204 collecting the PNAs each remain substantially the same during any continuous operation of the HPLC apparatus 200.

As illustrated in FIG. 6, the collector receptacles 204 containing the separately collected (a) aliphatic and monoaromatic compounds and (b) desorbing reagent-PNA combination are periodically emptied into the return conduit 48 and the desorbing reagent-PNA transporting conduit 52, respectively. For example, the collector receptacles 204 can be equipped with a drain valve (not shown) that is activated by a position locator device (not shown).

Accordingly, each time a collector receptacle 204 for aliphatic and monoaromatic compounds is positioned over the entrance (not shown) to the return conduit 48, the position locator device sends a signal that causes the drain valve of that receptacle 204 to open, thereby draining any aliphatic and aromatic compounds present in the receptacle 204 into the return conduit 48.

Similarly, each time a collector receptacle 204 for PNAs arrives over the entrance (not shown) to the desorbing reagent-PNA transporting conduit 52, the position locator device activates the drain valve of that receptacle 204, causing any PNAs present in the receptacle 204 to flow into the the desorbing reagent-PNA transporting conduit 52.

Any residual desorbing reagent present in the adsorbent bed 138' of FIG. 7 is removed from the bed 138' by the regenerator reagent stream which sequentially follows the desorbing reagent through the adsorbent 140. After removing any residual desorbing reagent and reactivating the adsorbent 140, the adsorption bed 138' is substantially fully regenerated and in essentially the same condition as it was at the beginning of the cycle. The cycle can be repeated as many times as necessary and, therefore, the process is continuous.

Although the present invention has been described in considerable detail with reference to several preferred versions, other versions are possible. For example, the stationary collector receptacles 106 of FIGS. 2 and 3 need not be employed in the adsorption apparatus 100, the aliphatic and monoaromatic compounds being allowed to flow directly into the entrances 172 of the return conduit 48 and the desorbing reagent-PNA combination being allowed to proceed straight into the entrances 174 of the desorbing reagent-PNA transporting conduit 52.

In addition, the adsorption bed, besides being annular, can also be linear. To illustrate, in an HPLC version of the invention, the adsorbent bed can be linear with the inlet tubes being linearly arranged in a rectangular inlet distribution manifold. Accordingly, sequentially synchronized intake multiposition valves and sequentially synchronized distributor multiposition valves are, as in the annular embodiment, computer programmed to sequentially and linearly (e.g., from right to left) advance the introduction of the recycle oil stream, the desorbing reagent stream, and the regenerator reagent stream into the adsorption bed through their respective grouping of inlet tubes. When any given stream reaches the last inlet tube on the left side of rectangular distributor manifold, that stream is then reintroduced into the first inlet tube on the right side of the manifold. In this fashion, the linear version of the invention maintains continuity.

In another embodiment of the invention, PNA-containing liquids other than recycle oil can be handled by the continuous PNA removal apparatus of the invention. Furthermore, in the HPLC version of the invention, the inlet tubes, in addition to being grouped into four quadrants, can be grouped into three or less sectors as well as five or more sectors. Also, other aspects and versions of continuous adsorption apparatus are described in U.S. Pat. No. 4,915,843 and application Ser. No. 07/402,533, filed Aug. 31, 1989.

In view of these other versions, the spirit and scope of the appended claims should not necessarily be limited to the description of the preferred versions contained herein.

What is claimed is:

1. A catalytic hydrocracking process comprising:
    (A) contacting a hydrocarbon feedstock in a hydrocracking zone with added hydrogen and a hydrocracking catalyst at a temperature and pressure sufficient to give a substantial conversion to lower boiling products; and
    (B) condensing a hydrocarbon effluent from the hydrocracking zone and separating the condensed effluent into (i) a low boiling hydrocarbon product and (ii) an unconverted hydrocarbon oil boiling above about 650° F. and containing one or more aliphatic compounds and one or more fused polynuclear aromatic compounds, the unconverted hydrocarbon oil then being fed as the feed mixture stream into a continuous chromatographic process comprising the steps of (a) simultaneously introducing a feed mixture stream, a desorbing reagent stream, and a regenerator reagent stream proximate the entrance end of an adsorbent bed, the feed stream comprising a mixture of aliphatic compounds and fused polynuclear aromatic compounds, wherein the compounds and fused polynuclear aromatic compounds, wherein the fused polynuclear aromatic compounds have a greater affinity than the aliphatic compounds for the bed, the desorbing stream comprises a liquid capable of removing the fused polynuclear aromatic compounds from the bed, and the regenerator stream comprises a gas capable of regenerating the bed, (b) moving the streams with respect to the bed, and (c) removing a first stream and a substantially separate second stream proximate the exit end of the bed, the first stream having a high concentration of aliphatic compounds with respect to the concentration of fused polynuclear aromatic compounds in the first stream and the second stream having a high concentration of fused polynuclear aromatic compounds with respect to the concentration of aliphatic compounds in the second stream.

2. The method of claim 1 further comprising the step (D) of recycling the aliphatic compounds exiting the adsorption bed to the hydrocracking zone.

3. The method of claim 1 further comprising the step (D) of delivering the aliphatic compounds exiting the adsorption bed to a different hydrocracking zone.

4. The method of claim 1 wherein the feed mixture stream, the desorbing reagent stream, and the regenerator reagent stream are simultaneously introduced at a pressure of at least about 100 psig each.

5. The method of claim 1 wherein step (b) includes the step of moving the streams with respect to the bed so that (I) substantially all of the bed is sequentially contacted with (i) the feed mixture stream, (ii) the desorbing reagent stream, and (iii) the regenerator reagent stream, and (II) substantially all the polynuclear aromatic compounds are sorbed onto the bed, substantially all the sorbed aromatic compounds then being removed from the bed by the desorbing reagent stream, and substantially all the desorbing reagent stream being removed from the bed by the regenerator reagent stream.

6. The method of claim 1 wherein step (a) includes the step of simultaneously introducing a purge reagent stream proximate the entrance end of the bed.

7. The method of claim 6 wherein step (b) includes the step of moving the streams with respect to the bed so that (I) the bed is sequentially contacted with (i) the feed mixture stream, (ii) the purge reagent stream, (iii) the desorbing reagent stream, and (iv) regenerator reagent stream, and (II) substantially all the polynuclear aromatic compounds are sorbed onto the bed, substantially all the sorbed aromatic compounds then being removed from the bed by the desorbing reagent stream, and substantially all the desorbing reagent stream being removed from the bed by the regenerator reagent stream.

8. The method of claim 7 wherein the purge reagent stream and regenerator reagent stream have substantially the same composition.

9. The method of claim 7 wherein the purge reagent stream and the regenerator reagent stream are both an inert gas.

10. The method of claim 1 further comprising the step (d) of recycling the desorbing reagent stream by removing a substantial portion of any polynuclear aromatic compounds in the desorbing reagent stream exiting the bed, thereby forming a recyclable desorbing reagent stream, and introducing the recyclable desorbing reagent stream proximate the entrance end of the bed.

11. The method of claim 1 further comprising the step (d) of recycling the desorbing reagent stream by removing a substantial portion of any polynuclear aromatic compounds in the desorbing reagent stream exiting the bed, thereby forming a recyclable desorbing reagent stream, and introducing the recyclable desorbing reagent stream proximate the entrance end of the bed, wherein the regenerator stream is a heated gas and step (b) includes the step of moving the streams with respect to the bed so that (I) substantially all of the bed is sequentially contacted with (i) the feed mixture stream, (ii) the desorbing reagent stream, and (iii) the regenerator reagent stream, and (II) substantially all the fused polynuclear aromatic compounds are sorbed onto the bed, substantially all the sorbed fused polynuclear aromatic compounds being removed from the bed by the desorbing reagent stream, and substantially all the desorbing reagent stream being removed from the bed by the regenerator reagent stream.

12. The method of claim 1 further comprising the step (d) of recycling the desorbing reagent stream by removing a substantial portion of any polynuclear aromatic compounds in the desorbing reagent stream exiting the bed, thereby forming a recyclable desorbing reagent stream, and introducing the recyclable desorbing reagent stream proximate the entrance end of the bed, wherein the regenerator stream is a heated gas, step (a) includes the step of simultaneously introducing a purge reagent stream proximate the entrance end of the bed, and step (b) includes the step of moving the streams with respect to the bed so that (I) substantially all of the bed is sequentially contacted with (i) the feed mixture stream, (ii) the purge reagent stream, (iii) the desorbing reagent stream, and (iv) the regenerator reagent stream, and (II) substantially all the fused polynuclear aromatic compounds are sorbed onto the bed, the purge reagent stream substantially preventing contact between the aliphatic compounds and the desorbing reagent stream, substantially all the sorbed fused polynuclear aromatic compounds being removed from the bed by the desorbing reagent stream, and substantially all the desorbing reagent stream being removed from the bed by the regenerator reagent stream.

13. The method of claim 1 wherein the adsorption bed has a plurality of substantially parallel, transverse ribs separating the bed into a plurality of substantially separate sections.

14. An oil refining process comprising:
(A) forming a liquid capable of solubilizing aromatic compounds having at least about 5 fused aromatic rings; and
(B) catalytically hydrocracking a hydrocarbon feedstock by:
  (i) contacting the feedstock in a hydrocracking zone with added hydrogen and a hydrocracking catalyst at a temperature and pressure sufficient to give a substantial conversion to lower boiling products; and
  (ii) condensing a hydrocarbon effluent from the hydrocracking zone and separating the condensed effluent into (AA) a low boiling hydrocarbon product and (BB) an unconverted hydrocarbon oil containing one or more fused polynuclear aromatic compounds, the unconverted hydrocarbon oil then being fed as the feed mixture stream into a continuous chromatographic process comprising the steps of (a) simultaneously introducing a feed mixture stream, a desorbing reagent stream, and a regenerator reagent stream proximate the entrance end of an adsorbent bed, the feed stream comprising a mixture of aliphatic compounds and fused polynuclear aromatic compounds, wherein the compounds and fused polynuclear aromatic compounds, wherein the fused polynuclear aromatic compounds have a greater affinity than the aliphatic compounds for the bed, the desorbing stream comprises a liquid capable of removing the fused polynuclear aromatic compounds from the bed, and the regenerator stream comprises a gas capable of regenerating the bed, (b) moving the streams with respect to the bed, and (c) removing a first stream and a substantially separate second stream proximate the exit end of the bed, the first stream having a high concentration of aliphatic compounds with respect to the concentration of fused polynuclear aromatic compounds in the first stream and the second stream having a high concentration of fused polynuclear aromatic compounds with respect to the concentration of aliphatic compounds in the second stream wherein at least a portion of the solvent formed in step (A) is used as the desorbing reagent stream.

15. A catalytic hydrocracking process comprising:
(A) contacting a hydrocarbon feedstock in a hydrocracking zone with added hydrogen and a hydrocracking catalyst at a temperature and pressure sufficient to give a substantial conversion to lower boiling products;
(B) condensing a hydrocarbon effluent from the hydrocracking zone and separating the condensed effluent into (i) a low boiling hydrocarbon product and (ii) an unconverted hydrocarbon oil boiling above about 650° F. and containing one or more aliphatic compounds and one or more fused polynuclear aromatic compounds;
(C) simultaneously introducing the unconverted hydrocarbon oil, a desorbing reagent stream, and a regenerator reagent stream proximate the entrance end of an adsorbent bed, wherein the fused polynuclear aromatic compounds in the unconverted hydrocarbon oil have a greater affinity than the aliphatic compounds in the unconverted hydrocarbon oil for the bed, the desorbing stream comprises a liquid capable of removing the fused polynuclear aromatic compounds from the bed, and the regenerator stream comprises a gas capable of regenerating the bed;

(D) moving the streams with respect to the bed; and (E) removing, proximate the exit end of the bed, a first stream having a high molar ratio of the aliphatic compounds to the fused polynuclear aromatic compounds and a second stream having a high molar ratio of the fused polynuclear aromatic compounds to the aliphatic compounds.

16. The method of claim 15 wherein the first stream is substantially devoid of the fused polynuclear aromatic compounds.

17. The method of claim 15 wherein the second stream is substantially devoid of the aliphatic compounds.

18. The method of claim 15 wherein the first stream is substantially devoid of the fused polynuclear aromatic compounds, and the second stream is substantially devoid of the aliphatic compounds.

* * * * *

UNITED STATES PATENT AND TRADEMARK OFFICE
CERTIFICATE OF CORRECTION

PATENT NO.   :   5,124,023

DATED         :   June 23, 1992

INVENTOR(S) :   Paula J. Bosserman and Vernon T. Taniguchi

It is certified that error appears in the above-identified patent and that said Letters Patent is hereby corrected as shown below:

Claim 1, column 14, lines 18 and 19, delete "compounds and fused polynuclear aromatic compounds, wherein the".

Claim 14, column 16, lines 22-24, delete "compounds and fused polynuclear aromatic compounds, wherein the".

Signed and Sealed this

Seventeenth Day of August, 1993

Attest:

BRUCE LEHMAN

Attesting Officer

Commissioner of Patents and Trademarks